US011478416B2

(12) United States Patent
Pereira et al.

(10) Patent No.: US 11,478,416 B2
(45) Date of Patent: Oct. 25, 2022

(54) INGREDIENTS FOR USE IN PERSONAL CARE COMPOSITIONS

(71) Applicant: Croda, Inc., Edison, NJ (US)

(72) Inventors: Abel Pereira, Bridgewater, NJ (US); Christina Bishop, Clifton, NJ (US); Steven Jez Uzupis, South Bound Brook, NJ (US); Farahdia Edouard, Edison, NJ (US); Marni Dexter, Cranford, NJ (US); Erik Gunderman, Flemington, NJ (US)

(73) Assignee: Croda Inc., Plainsboro, NJ (US)

( * ) Notice: Subject to any disclaimer, the term of this patent is extended or adjusted under 35 U.S.C. 154(b) by 0 days.

(21) Appl. No.: 16/465,625

(22) PCT Filed: Oct. 23, 2017

(86) PCT No.: PCT/US2017/057875
§ 371 (c)(1),
(2) Date: May 31, 2019

(87) PCT Pub. No.: WO2018/102050
PCT Pub. Date: Jun. 7, 2018

(65) Prior Publication Data
US 2019/0314265 A1    Oct. 17, 2019

Related U.S. Application Data

(60) Provisional application No. 62/428,722, filed on Dec. 1, 2016.

(51) Int. Cl.
| *A61K 8/84* | (2006.01) |
| *A61K 8/36* | (2006.01) |
| *A61K 8/41* | (2006.01) |
| *A61Q 5/06* | (2006.01) |
| *A61Q 5/12* | (2006.01) |
| *A61K 8/49* | (2006.01) |

(52) U.S. Cl.
CPC ............... *A61K 8/84* (2013.01); *A61K 8/361* (2013.01); *A61K 8/41* (2013.01); *A61Q 5/06* (2013.01); *A61Q 5/12* (2013.01); *A61K 8/4973* (2013.01)

(58) Field of Classification Search
None
See application file for complete search history.

(56) References Cited

U.S. PATENT DOCUMENTS

| 3,090,737 | A |   | 5/1963 | Swartz |
| 4,626,429 | A | * | 12/1986 | Robbins ............ A61Q 5/12 424/70.17 |
| 5,747,108 | A |   | 5/1998 | Farooq et al. |
| 6,004,914 | A |   | 12/1999 | Perella et al. |
| 6,365,142 | B1 |   | 4/2002 | Tamura |
| 6,369,007 | B1 |   | 4/2002 | Perella et al. |
| 6,388,111 | B1 | * | 5/2002 | Pereira ............ A61K 8/416 554/56 |
| 6,432,895 | B1 |   | 8/2002 | Bigorra et al. |
| 6,500,791 | B2 |   | 12/2002 | Pereira et al. |
| 7,824,667 | B2 |   | 11/2010 | Queralt et al. |
| 8,231,864 | B2 |   | 7/2012 | Grandmaire et al. |
| 2004/0146478 | A1 |   | 7/2004 | Queralt et al. |
| 2013/0225470 | A1 |   | 8/2013 | Allen et al. |

FOREIGN PATENT DOCUMENTS

| EP | 0038862 A1 | 11/1981 |
| EP | 0875500 A2 | 11/1998 |
| EP | 1254653 A1 | 11/2002 |
| EP | 1037599 B1 | 10/2004 |
| EP | 1117634 B1 | 2/2006 |
| EP | 1254654 B2 | 6/2008 |
| EP | 1902083 B1 | 10/2010 |
| EP | 2764860 A1 | 8/2014 |
| JP | 06345704 A | 12/1994 |
| JP | 2000178145 A | * 6/2000 |
| JP | 2000198721 A | 7/2000 |
| JP | 2003081776 A | 3/2003 |
| JP | 2010077061 A | 4/2010 |
| WO | 0020380 A1 | 4/2000 |
| WO | 2013005025 A2 | 1/2013 |
| WO | WO 2013/005025 | * 1/2013 |
| WO | WO 2013005025 | * 1/2013 |

OTHER PUBLICATIONS

International Search Report and Written Opinion for International Application No. PCT/US2017/057875, dated Jan. 9, 2018—12 pages.

Zhang et al., "Quaternary Ammonium Compounds (QACs): A Review on Occurrence, Fate and Toxicity in the Environment", Science of the Total Environment, Jun. 15, 2015, 518-519—pp. 352-362.

International Preliminary Report on Patentability and Written Opinion for International Application No. PCT/US2017/057875, dated Jun. 4, 2019—10 pages.

Japanese Notice of Reasons for Refusal for Japanese Application No. 2019-529163, dated Jun. 29, 2021, with translation, 9 pages.

Japanese Notice of Reasons for Refusal for Japanese Application No. 2019-529163, dated Apr. 25, 2022 with translation, 5 pages.

* cited by examiner

*Primary Examiner* — Danah Al-Awadi
(74) *Attorney, Agent, or Firm* — RatnerPrestia

(57) ABSTRACT

A dialkyl amidoamine which is the reaction product of a polyamine, a monocarboxylic acid, or a triglyceride or derivative thereof, and optionally an epoxide-containing compound is described. The dialkyl amidoamine may be used as a conditioning agent or anti-frizz agent useful in personal care applications, particularly in the conditioning of hair. The preparation and use of a conditioning agent and an anti-frizz agent comprising the dialkyl amidoamine are also described.

22 Claims, No Drawings

INGREDIENTS FOR USE IN PERSONAL CARE COMPOSITIONS

CROSS REFERENCE TO RELATED APPLICATIONS

This application is the National Stage filing of International Appln. No. PCT/US2017/057875, filed Oct. 23, 2017, and claims priority under 35 U.S.C. § 119(e) to U.S. Provisional Patent Application No. 62/428,722, filed Dec. 1, 2016, the entirety of which applications is hereby incorporated herein by reference.

TECHNICAL FIELD

The present invention relates to chemical ingredients and their use in personal care formulations, in particular in hair care formulations. More particularly, the present invention relates to conditioning agents and anti-frizz agents for use in hair care compositions. The chemical ingredients described define a class of dialkyl amidoamines comprising the reaction product(s) of a polyamine, a fatty acid and an epoxyalkane, and their use as a conditioning agent and as an anti-frizz agent.

BACKGROUND ART

Quaternary ammonium compounds, including dialkyl quaternary amidoamine compounds, have long been known and are said to be used as conditioning agents for personal care compositions, in particular hair conditioners, shampoos and conditioning shampoos. Quaternary ammonium compounds are positively charged species (cationic species) which are attracted to negatively charged, damaged protein sites on hair fibres, thus remaining on the hair by electrostatic charges and imparting a conditioning effect.

However, it is generally understood that quaternary ammonium compounds do not have a particularly good environmental profile, for example they are not known to have good aquatic toxicity. Recent studies, including "Quaternary ammonium compounds (QACs): a review on occurrence, fate and toxicity in the environment", Zhang C et al., Sci Total Environ, 2015 Jun. 15; 518-519; 352-62, have shown that quaternary ammonium compounds are toxic to a lot of aquatic organisms including fish, daphnids, algae, rotifer and microorganisms employed in wastewater treatment systems. This is particularly problematic since most uses of quaternary ammonium compounds can be expected to lead to their release to wastewater treatment plants and then dispersed into various environmental compartments through sewage effluent and sludge land application.

Therefore, there is a need for the development of conditioning agents which still offer a good conditioning effect, but which do not suffer from the same environmental profile, or aquatic toxicity inadequacies as quaternary ammonium compounds.

SUMMARY OF THE INVENTION

It is an object of the present invention to address the above and/or other disadvantages associated with the prior art.

According to an aspect of the present invention, there is provided a conditioning agent comprising at least 50% by weight based on the total weight of the conditioning agent of a dialkyl amidoamine which is the reaction product of a) a polyamine;
b) a monocarboxylic acid, or a derivative thereof, having a carbon chain length of from 12 to 28; and
c) optionally, an epoxide-containing compound.

According to another aspect of the present invention, there is provided a predispersion or presolution comprising a conditioning agent comprising at least 50% by weight based on the total weight of the conditioning agent of a dialkyl amidoamine which is the reaction product of a) a polyamine;
b) a monocarboxylic acid, or a derivative thereof, having a carbon chain length of from 12 to 28; and
c) optionally, an epoxide-containing compound;
and a dispersing agent or solvent or mixture thereof.

Particularly, there is provided a conditioning agent which comprises at least 60% by weight based on the total weight of the conditioning agent of the dialkyl amidoamine, preferably at least 70% by weight, more preferably at least 80% by weight based on the total weight of the conditioning agent of the dialkyl amidoamine.

The term conditioning agent refers to an ingredient for a personal care composition, preferably a skin care or hair care composition, particularly a hair care composition, which provides a soft feel and texture to the skin or hair.

By 'polyamine', it is meant any molecule comprising at least 2 nitrogen atoms.

Preferably, the dialkyl amidoamine is tertiary. This term assumes its normal meaning within the art. By this, it should be understood that the amine nitrogen in the amidoamine is tertiary, i.e. directly bonded to three organic substituents other than hydrogen.

Preferably, the conditioning agent is substantially free from quaternary ammonium compounds. By the use of the term "substantially free from", it is meant that the conditioning agent comprises preferably less than 10% by weight of quaternary ammonium compounds, preferably less than 5% by weight, more preferably less than 2% by weight and most preferably, less than 1% by weight based on the total weight of the conditioning agent. Preferably, the conditioning agent comprises no quaternary ammonium compounds.

Preferably, the conditioning agent comprises no quaternary ammonium compounds which may be produced by quaternising the reaction product of the a) a polyamine;
b) a monocarboxylic acid, or a derivative thereof, having a carbon chain length of from 12 to 28; and
c) optionally, an epoxide-containing compound.

According to a further aspect of the present invention, there is provided the use of a dialkyl amidoamine which is the reaction product of a) a polyamine;
b) a monocarboxylic acid, or a derivative thereof, having a carbon chain length of from 12 to 28; and
c) optionally, an epoxide-containing compound;
as a conditioning agent.

The dialkyl amidoamine may be used as a conditioning agent for a personal care formulation. Particularly, there is provided the use of the dialkyl amidoamine as a conditioning agent for conditioning hair, more particularly as a conditioning agent in a hair conditioning formulation. Preferably, the dialkyl amidoamine may be used as a conditioning agent in the place of, or instead of, a quaternary ammonium compound. More preferably, the dialkyl amidoamine is used as a conditioning agent in a hair conditioning formulation which does not contain a quaternised ammonium compound. Desirably, there is provided the use of the dialkyl amidoamine as a hair conditioning agent in a hair conditioning formulation which does not contain any quaternised ammonium compounds having an alkyl group with a carbon chain which is the same length as that of the monocarboxylic acid or derivative thereof.

According to yet another aspect of the present invention, there is provided a method of conditioning hair, comprising applying a conditioning agent to the hair, wherein the conditioning agent comprises at least 50% by weight based on the total weight of the conditioning agent of a dialkyl amidoamine which is the reaction product of
  a) a polyamine;
  b) a monocarboxylic acid, or a derivative thereof, having a carbon chain length of from 12 to 28; and
  c) optionally, an epoxide-containing compound.

The present invention also extends to an anti-frizz agent. The anti-frizz agent is a dialkyl amidoamine which is the reaction product of
  a) a polyamine;
  b) a monocarboxylic acid, or a derivative thereof, having a carbon chain length of from 12 to 28; and
  c) optionally, an epoxide-containing compound.

There is also provided a method of reducing frizz in hair comprising applying the anti-frizz agent to the hair, and the use of a dialkyl amidoamine which is the reaction product of
  a) a polyamine;
  b) a monocarboxylic acid, or a derivative thereof, having a carbon chain length of from 12 to 28; and
  c) optionally, an epoxide-containing compound;
as an anti-frizz agent.

By the term anti-frizz agent, it is meant an ingredient for a hair care composition, which is operable to reduce the amount of frizz in the hair. By the use of the term frizz in the present application, it is meant the tendency of naturally curly hair which has been smoothed or straightened to revert to a curly or tight curly state, usually due to exposure to high humidity.

DETAILED DESCRIPTION

The dialkyl amidoamine of the present invention is preferably obtained by the reaction of a) a polyamine; b) a monocarboxylic acid, or a derivative thereof, having a carbon chain length of from 12 to 28; and c) optionally, an epoxide-containing compound. Preferably, the dialkyl amidoamine is the reaction product of a polyamine, a monocarboxylic acid, or a derivative thereof, having a carbon chain length of from 12 to 28, and an epoxide-containing compound.

By the use of the term "polyamine" in the present specification, it is meant a compound comprising two or more amine groups, preferably three or more amine groups. The amine groups present in the polyamine may be independently primary, secondary or tertiary. Preferably, the terminal amine groups in the polyamine are primary and the remainder of the amine groups secondary or tertiary.

Preferably, the polyamine has the general structure $R^3_2N-[R^2-N(R)]_n-R^4$.

Each $R^1$ is preferably a moiety independently selected from the group comprising —H, a lower alkyl group or a lower alkylene group operable to bond with another N atom in the polymer chain. Preferably, each $R^1$ is either —H or a lower alkyl group, preferably methyl, ethyl or propyl, more preferably —H. The $R^1$ moieties may be the same as each other or different from each other. Preferably, all the $R^1$ moieties are the same as each other.

Each $R^2$ is independently preferably a lower alkylene moiety, preferably a methylene, ethylene, propylene or butylene moiety, more preferably a methylene or ethylene moiety, most preferably an ethylene moiety. Each of the $R^2$ moieties may be the same as each other or different from each other. Preferably, all the $R^2$ moieties are the same as each other.

Each $R^3$ moiety is independently selected from the group comprising —H and lower alkyl, most preferably —H. $R^4$ is preferably selected from the group comprising —H and lower alkyl, more preferably —H. The $R^3$ and $R^4$ moieties may be the same as each other or different from each other. Preferably, all the $R^3$ and $R^4$ moieties are the same as each other, most preferably —H.

n is preferably an integer between 1 and 20, preferably between 1 and 12, more preferably between 2 and 8 and most preferably between 2 and 5.

By the use of the term "lower alkylene" in the present specification, it is meant any moiety having the general structure $-C_mH_{2m}-$, wherein m is an integer between 1 and 20, preferably between 1 and 15, preferably between 1 and 10 and most preferably between 1 and 6.

By the use of the term "lower alkyl" in the present specification, it is meant any moiety having the general structure $-C_mH_{2m+1}$, wherein m is an integer between 1 and 20, preferably between 1 and 15, preferably between 1 and 10 and most preferably between 1 and 6.

Preferably, the polyamine of the invention has a molecular weight of up to 1000 Daltons, preferably up to 700 Daltons, more preferably up to 500 Daltons and most preferably up to 300 Daltons, and of at least 50 Daltons, more preferably at least 100 Daltons, most preferably at least 150 Daltons.

The polyamine may comprise one or more cyclic moieties. Cyclic moieties may be present in either linear or branched polyamines. Preferably, cyclic moieties in the polyamines are effected when an $R^1$ group is a lower alkylene moiety and bonds to another N atom in the polymer chain, preferably an N atom in an adjacent repeating unit of the polyamine. Preferably, when the polyamine comprises a cyclic moiety, it is a piperazine moiety. Alternatively, cyclic moieties may be formed from cross-linking between $R^1$, $R^2$, $R^3$ and/or $R^4$ groups, preferably between $R^1$ and $R^2$ moieties.

Preferably, the polyamine selected from the group comprising diethylene triamine (DETA), triethylene tetramine (TETA), tetraethylene pentamine (TEPA), pentaethylene hexamine and methylamino dipropylamine. Preferably, the polyamine is diethylene triamine or methylamino dipropylamine, most preferably diethylene triamine.

A mixture of polyamines may be present in the active compound of the invention. In this case, the mixture may comprise branched polyamines, linear polyamines, or a mixture thereof.

Monocarboxylic acids suitable for use herein are preferably fatty acids. The derivatives of the monocarboxylic acids may suitably be in the form of triglycerides, methyl esters or ethyl esters.

When used herein, the term triglyceride refers to a triester of glycerol with three monocarboxylic acid units. The monocarboxylic acid units present in the triglyceride may be the same as each other or they may be different. Preferably, the triglycerides used herein are naturally occurring.

Monocarboxylic acids and derivatives thereof suitable for use in the present invention can be obtained from natural sources such as, for example plant or animal oils and/or waxes. For example, the acids and/or derivatives thereof, particularly triglycerides, may be obtained from palm oil, rape seed oil, HEAR (high erucic acid rape) oil, palm kernel oil, coconut oil, babassu oil, soybean oil, castor oil, sunflower oil, olive oil, linseed oil, cottonseed oil, safflower oil, tallow, whale or fish oils, grease, lard, jojoba oil (fatty acids and fatty alcohols), tribehenin, montan wax, lanolin acids including 18MEA, and mixtures thereof.

The monocarboxylic acid may also be synthetically prepared. Relatively pure unsaturated acids such as oleic acid, linoleic acid, linolenic acid, palmitoleic acid, and elaidic acid may be isolated, or relatively crude unsaturated fatty acid mixtures employed.

Of course, it is possible in accordance with the present invention to use pure fatty acids and/or artificially created mixtures including, without limitation arachidic acid, behenic acid, isobehenic acid, stearic acid, isostearic acid, palmitic acid, isopalmitic acid, gadoleic acid, erucic acid, arachidonic acid and culpodonic acid. Mixtures of fatty acids are also possible which include fatty acid constituents of lower carbon chain lengths.

Resin acids, such as those present in tall oil, may also be used.

Preferably, the monocarboxylic acid, and/or the monocarboxylic acids units in the triglyceride have at least 14 carbon atoms, preferably at least 16 carbon atoms. Preferably, the monocarboxylic acid, and/or the monocarboxylic acids units in the triglyceride have up to 24 carbon atoms, preferably up to 22 carbon atoms.

The monocarboxylic acid or triglyceride may be in derivative form, for example as a salt, such as an acid chloride. Such derivatives will usually be naturally occurring and present in combination with the acids or triglycerides described above.

Positive results have been seen by the inventors when using saturated, monounsaturated and polyunsaturated monocarboxylic acids and derivatives thereof, either alone or in any combination. It has also surprisingly been found that positive results can be achieved by using linear and branched monocarboxylic acids and derivatives thereof, either alone or in any combination.

It is preferred that the monocarboxylic acid or derivative thereof is a mixture of monocarboxylic acids or derivatives thereof. The mixture may comprise monocarboxylic acids or derivatives thereof with different degrees of unsaturation and/or different degrees of branching. Preferably, the mixture of monocarboxylic acids or derivatives thereof comprises some monounsaturated and/or polyunsaturated acid, such as oleic and/or linoleic acid.

Reference is made herein to the use of monocarboxylic acids, or derivatives thereof, having a specified carbon chain length. If a 100% pure, artificially created acid is used, then 100% of the monocarboxylic acid constituents of the amidoamines will have the specified carbon chain length. If a naturally occurring oil/wax or relatively crude monocarboxylic acid mixture is used, then it is possible that not all of the monocarboxylic acids or derivatives thereof, and therefore the resulting amidoamines, will have a carbon chain length of the specified length. As should be clear, this means that the monocarboxylic acid or derivative thereof can be made up of one or more monocarboxylic acids or derivatives thereof, at least a significant proportion of which will have a carbon chain length of the specified length, preferably the significant proportion will be at least 30%, preferably at least 50%.

The oils or any of the pure acids contained in them should have, most preferably, but not absolutely necessary, a melt point of 100° C. or less and more preferably 85° C. or less.

Where DETA is used as the polyamine, it should be understood that in the resulting dialkyl amidoamine product, two of the three nitrogen atoms in each DETA molecule will be bonded to an alkyl chain via an amide bond after the reaction with the monocarboxylic acid or derivative thereof.

The remaining nitrogen molecule will be an amine nitrogen. Either the nitrogen in the first, second or third position along the DETA chain can be the amine nitrogen. The remaining two nitrogen atoms in the DETA molecule would be bound to the alkyl chains (they would be amido nitrogens). Therefore, it is possible to produce a dialkyl amidoamine which is either symmetric about the second nitrogen, or unsymmetric. It is expected that the final product would be a mixture of symmetric and unsymmetric dialkyl amidoamines.

The skilled person will appreciate that the above description can apply analogously to situations where polyamines other than DETA are used.

Preferably, the dialkyl amidoamine is a tertiary dialkyl amidoamine, meaning that the amine nitrogen is a tertiary amine. The term 'tertiary' will be appreciated by the person skilled in the art to take its normal meaning within the art, i.e. that the amine nitrogen is substituted with three organic groups other than hydrogen.

In a polyamine of the type like methylamino dipropylamine, the amine nitrogen is already a tertiary amine. In this embodiment, the dialkyl amidoamine is the reaction product of a polyamine and a monocarboxylic acid, or a derivative thereof, having a carbon chain length of from 12 to 28. More particularly, in this embodiment, no epoxide-containing compound is required.

Where $R^1$ is —H, the amine nitrogen is a secondary amine. In this embodiment, the dialkyl amidoamine is the reaction product of a polyamine; a monocarboxylic acid, or a derivative thereof, having a carbon chain length of from 12 to 28; and an epoxide-containing compound. The epoxide-containing compound reacts with the hydrogen atom of the secondary amine group to give a tertiary amine.

The epoxide-containing compound may be an epoxide (alkylene oxide), an epoxy alcohol or an epoxy ether. Preferably, the epoxide-containing compound is selected from the group comprising epoxy alcohols such as glycidol; alkylene oxides such as ethylene oxide, propylene oxide; and epoxy ethers such as glycidyl ethers including those having the formula

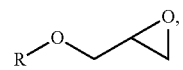

where R can be either an alkyl group having a carbon chain length of from 2 to 22, or a methyl-capped PEG such as $CH_3$—O—$(CH_2CH_2O)_n$ where n is an integer from 1 to 20. Most preferably, the epoxide-containing compound is an alkylene oxide or epoxy alcohol, most preferably selected from the group comprising glycidol, ethylene oxide and propylene oxide.

It can be useful for the amine nitrogen to be bonded to an electronegative group, for example an epoxide-containing compound, in order to render the resulting dialkyl amidoamines compatible with anionic surfactants. Electronegative groups suitable for this purpose can include, but are not limited to, alkoxy groups, such as ethoxy groups and propoxy groups; hydroxy groups, such as OH and dihydroxy alkyl groups; aldehydes; acids; polyethyoxy groups (polyalkoxy groups); glycidol groups; and the like.

Preferably, the dialkyl amidoamines of the present invention comprise a relatively simple ratio of polyamine to monocarboxylic acid or derivative thereof to epoxide-containing compound of 1:2:1, or a ratio of polyamine to triglyceride or derivative thereof to epoxide-containing compound of 3:2:3.

In an alternative embodiment, the epoxide-containing compound could be replaced with between 2 and 20 alkylene oxide units. In such a case, the polyamine, monocarboxylic acid or derivative thereof and epoxide-containing compound components are preferably present in the dialkyl amidoamine at a molar ratio of 1:2:2-20. Alternatively, the polyamine, triglyceride or derivative thereof and epoxide-containing compound components are preferably present in the dialkyl amidoamine at a molar ratio of 3:2:6-60.

The dialkyl amidoamine of the present invention may be produced by a straightforward one- or two-step process involving the esterification of a polyamine and monocarboxylic acid or derivative thereof, followed, where applicable, by the reaction of the ester with an epoxide-containing compound.

In the esterification reaction, the polyamine and monocarboxylic acid reactants are introduced to a pressure vessel and reacted at an elevated temperature, preferably between 80° C. and 250° C., i.e. above the melting temperature of the monocarboxylic acid or derivative thereof. The acid value and/or base value of the reaction mixture may be measured at intervals during the reaction process, and the reaction stopped once a required value is reached. Preferably, the reaction will continue until an acid value of <10 mg KOH is reached, and more preferably <5 mg KOH. The acid value and may be measured by titrating with a hydrochloric acid solution of known Normality to a Phenolphthalein endpoint, or by autotitrator as known to the person skilled in the art.

If required, the produced dialkyl amidoamine is further reacted with an epoxide-containing compound. This reaction preferably takes place in a pressure vessel at an elevated temperature of between 80° C. and 200° C. The epoxide-containing compound is added to the dialkyl amidoamine in the pressure vessel until the tertiary amine content is greater than 95%. The tertiary amine content may be measured according to the standard method described in AOCS Tf 3a-64 ("Percent Primary, Secondary, and Tertiary Amines in Fatty Amines").

The dialkyl amidoamine according to the present invention may be neutralised. By 'neutralised' it is meant that the pH of the dialkyl amidoamine is modified to between 3 and 7, more preferably between 4 and 6. Suitable neutralization agents include organic or inorganic acids, such as L-glutamic acid, lactic acid, hydrochloric acid, sulphuric acid, malic acid, succinic acid, acetic acid, fumaric acid, 1-glutamic acid hydrochloride, tartaric acid, oleic acid, isostearic acid, lanolin acids, mono- or di-alkyl phosphate ester, and mixtures thereof.

The dialkyl amidoamine of the present invention may be used as a conditioning agent.

Preferably, the conditioning agent is a hair conditioning agent, more preferably a human hair conditioning agent. The conditioning agent may be used as the, or one of the, active ingredient(s) in a personal care formulation, preferably a hair conditioning formulation.

The conditioning agent of the present invention preferably comprises a dialkyl amidoamine which is the reaction product of a polyamine, a monocarboxylic acid, triglyceride or derivative thereof and an epoxide-containing compound. Preferably, the conditioning agent comprises the dialkyl amidoamine of the present invention. The dialkyl amidoamine of the present invention is preferably present in the conditioning agent at a concentration of at least 60% by weight based on the total weight of the conditioning agent, preferably at least 70%, more preferably at least 80% and desirably at least 90% by weight based on the total weight of the conditioning agent. Preferably, the conditioning agent consists essentially of the dialkyl amidoamine described above.

The conditioning agent preferably does not contain any quaternised dialkyl amidoamine compounds. Significantly, the conditioning agent does not comprise any quaternised dialkyl amidoamine compounds having an alkyl group with a carbon chain which is the same length as that of the monocarboxylic acid, triglyceride or other derivative thereof.

Preferably, the conditioning agent is anhydrous. By the term anhydrous, it is meant that the conditioning agent preferably comprises a maximum of 10% by weight water. More preferably, the conditioning agent comprises a maximum of 7% by weight water, most preferably, 5% and desirably 2% by weight. Preferably, the conditioning agent comprises 0.01% to 10% by weight water, preferably 0.05% to 5%, most preferably 0.1% to 2% by weight.

The dialkyl amidoamine of the present invention may alternatively be used as an anti-frizz agent. The anti-frizz agent of the present invention preferably consists essentially of the dialkyl amidoamine described above.

Preferably, the anti-frizz agent is anhydrous. By the term anhydrous, it is meant that the anti-frizz agent preferably comprises a maximum of 10% by weight water. More preferably, the anti-frizz agent comprises a maximum of 7% by weight water, most preferably, 5% and desirably 2% by weight. Preferably, the anti-frizz agent comprises 0.01% to 10% by weight water, preferably 0.05% to 5%, most preferably 0.1% to 2% by weight.

The anti-frizz agent may be used as the, or one of the, active ingredient(s) in a personal care formulation, preferably a hair conditioning formulation. The anti-frizz agent may be used in a personal care composition together with other conditioning agents, or without the need for additional conditioning agents.

The conditioning agent or anti-frizz agent may be dispersed or dissolved in a predisperion or presolution, respectively, for ease of manufacture, storage, transportation and/or formulation.

In such a case, preferably the predispersion or presolution comprises the conditioning agent or anti-frizz agent and a dispersant or solvent, respectively. Preferably, the conditioning agent or anti-frizz agent is present in the predispersion or presolution at a concentration of at least 15% by weight based on the total weight of the predispersion or presolution, preferably at least 25%, more preferably at least 35% by weight based on the total weight of the predispersion or presolution. Preferably, the conditioning agent or anti-frizz agent is present in the predispersion or presolution at a concentration of up to 90% by weight based on the total weight of the predispersion or presolution, preferably at least 75%, more preferably at least 60% by weight based on the total weight of the predispersion or presolution.

The dispersant or solvent may be a fatty alcohol. Non-limiting examples of suitable dispersants or solvents may be cetyl alcohol, stearyl alcohol, behenyl alcohol, glycols such as di-ethylene glycol, propylene glycol, di-propylene glycol and propane diol, isostearyl alcohol, isobehenyl alcohol, isocetyl alcohol, and combinations thereof. Preferably, the dispersant or solvent is cetyl alcohol, stearyl alcohol or behenyl alcohol.

The dispersant or solvent may be used to aid formulation. For example, the dispersant or solvent may dilute a waxy solid and impart structure, or to thin out a gel-type product.

The conditioning agent or anti-frizz agent may be used as a conditioning agent or anti-frizz agent, respectively, for a personal care formulation. The personal care formulation may be a skin care or hair care formulation. Preferably, the personal care formulation is a hair care formulation. More preferably, the personal care formulation is a hair cleansing, conditioning, de-tangling, colour-protecting or styling formulation. More preferably, the personal care formulation is a friction modifying formulation operable to reduce the surface friction of human or animal hair fibres.

The personal care formulations of the type defined herein may be in the form of oil in water emulsions; water in oil emulsions; anhydrous formulations, including hair oils, hair sprays/serums; detergent formulations; more particularly in personal care emulsion formulations such as oil in water emulsions and detergent formulations. Personal care emulsion formulations can take the form of pastes, creams, liquids and milks desirably, and in the field of hair care formulations aim to provide a pleasant aesthetic feel to the hair as well as improving manageability and visual appearance.

The personal care formulation may have a range of different consistencies and/or viscosities depending on the desired end use of the formulation.

The end use applications of such formulations include, in the field of personal care products, moisturizers, body butters, gel creams, high perfume containing products, perfume creams, hair conditioners, hair relaxer formulations, hair shampoos, hair styling products, leave-on hair products, water-free products, anti-perspirant and deodorant products, cleansers, 2-in-1 foaming emulsions, emulsifier free products, mild formulations, scrub formulations e.g. containing solid beads, silicone in water formulations, pigment containing products, sprayable emulsions such as hair detanglers, colour cosmetics, shower products, make-up remover, eye make-up remover, and wipes. More preferably, the end use applications of such formulations include hair conditioners, hair relaxer formulations, hair shampoos, hair styling products, leave-on hair products and sprayable emulsions such as hair detanglers.

Personal care emulsion formulations comprising the conditioning agents of the present invention may include various other personal care ingredients. For example, suitable other ingredients include one or more ingredients such as cleansing agents, hair conditioning agents, skin conditioning agents, hair styling agents, antidandruff agents, hair growth promoters, perfumes, sunscreen compounds, pigments, moisturizers, film formers, humectants, alpha-hydroxy acids, hair colours, make-up agents, detergents, thickening agents, antiseptic agents, deodorant actives and surfactants.

Preferably, no further active conditioning ingredients are needed in the personal care formulation. Preferably, the conditioning agent described above is the only active conditioning ingredient present in the personal care formulation. Preferably, the formulation is free from additional conditioning components, for example quaternised ammonium compounds or silicones.

Preferably, no further anti-frizz agents are needed in the personal care formulation. Preferably, the anti-frizz agent described above is the only active anti-frizz ingredient present in the personal care formulation.

Preferably, the conditioning agent or anti-frizz agent is present at a low concentration in the personal care formulation. Preferably, the conditioning agent or anti-frizz agent is present in the formulation at a concentration of at least 0.01% w/w, preferably at least 0.1% w/w, more preferably at least 0.5% w/w and most preferably at least 0.8% w/w based on the total weight of the formulation. Preferably, the conditioning agent or anti-frizz agent is present in the formulation at a concentration of up to 5% w/w, preferably up to 4% w/w, more preferably up to 3% w/w and most preferably up to 2% w/w based on the total weight of the formulation.

Preferably, the personal care formulation comprises a base vehicle to carry the conditioning agent or anti-frizz agent. Preferably, the base vehicle comprises a relatively high concentration of water. Preferably, water is present in the personal care formulation at a concentration of at least 20% w/w, preferably at least 25% w/w, more preferably at least 28% w/w and most preferably at least 30% w/w of the total formulation. Preferably, water is present in the personal care formulation at a concentration of up to 99.9% w/w, preferably up to 99% w/w, preferably, up to 98% w/w and most preferably up to 97% w/w of the total formulation.

Preferably, the personal care formulation is acidic. Preferably the formulation has a pH of between 1 and 6, preferably between 2 and 5.5, more preferably of between 3 and 5, and most preferably of between 4 and 4.5.

The personal care formulation may comprise additional components, for example, additional emollients, carriers, surfactants and the like.

Preferably, the personal care formulation further comprises an emulsifier. Preferably, the emulsifier is a non-ionic, high HLB (hydrophilic/lipophillic balance) surfactant which is capable of forming an oil-in-water emulsion. The emulsifier may be naturally derived. Examples of suitable emulsifiers include ethoxylated sorbitan esters, ethoxylated glyceryl esters, ethoxylated fatty alcohols (including lanolin alcohols), ethoxylated fatty acids (including lanolin fatty acids), glycerol fatty acid mono-esters, glycol fatty acid mono and di-esters, sugar esters (fatty acid mono and di esters of sucrose), fatty acid polyol (polyethylene glycol) esters, fatty alcohols (which may also act as co-emulsifiers), fatty acids and/or phosphate esters thereof, cationic surfactants or monoalkyl tertiary amines such as stearamidopropyl dimethylamine or behenamidopropyl dimethylamine.

When present in the formulation, the emulsifier is preferably present at a concentration of at least 0.2% w/w, preferably at least 0.5% w/w, more preferably at least 0.9% w/w and most preferably at least 1.1% w/w based on the total weight of the formulation. Preferably, the emulsifier is present in the formulation at a concentration of up to 20% w/w, preferably up to 12% w/w, more preferably up to 7% w/w and most preferably up to 5% w/w based on the total weight of the formulation. The concentration of emulsifier present in the formulation is preferably higher than that present in a formulation of this type comprising quaternised materials. This is to compensate for the absence of quaternised materials in the formulation which would usually have an emulsifying effect on the formulation.

The personal care formulation may further comprise at least one co-emulsifier. Preferably, the or each co-emulsifier is a viscosity modifier, able to modify the viscosity of the formulation, more preferably a viscosity builder, able to increase the viscosity of the formulation. Preferably, the or each co-emulsifier is a fatty alcohol, preferably a $C_{12}$ to $C_{20}$ alcohol, more preferably a $C_{16}$ to $C_{18}$ alcohol, or a mixture thereof. Suitable alcohols for use as co-emulsifiers in the personal care formulation include cetyl alcohol, stearyl alcohol and cetearyl alcohol.

The formulations according to the present invention may also contain other additional emollient materials, preferably emollient oils. Preferably, the emollient oil is a non-polar oil. Examples of emollient oils which are suitable for use in the present formulation include mineral or paraffin oil; esters of fatty acids and fatty alcohols, preferably $C_{10}$-$C_{20}$ acids or alcohols, although isopropyl esters may be used; fatty acid glycol esters; fatty acid triglycerides; esters and diesters of alkoxylated fatty alcohols; botanical (plant) extracts; and hydrocarbons, preferably $C_{12}$-$C_{16}$. Preferably, the emollient is mineral oil. When present in the formulation, the or each additional emollient is preferably present at a concentration of at least 1% and up to 30% by weight based on the total weight of the formulation.

The personal care formulation according to the present invention may also contain one or more surfactants, for example sodium lauryl ether sulphate or cocamidopropyl betaine. When present in the formulation, the or each surfactant is preferably present at a concentration of between 1% and 20%, preferably between 2% and 15% and more preferably between 4% and 10% by weight based on the total weight of the formulation.

The personal care formulation according to the present invention may also contain one or more proteins or derivatised proteins. When present in the formulation, the or each protein or derivatised protein is preferably present at a concentration of between 0.1% and 10%, preferably between 0.5% and 8% and more preferably between 1% and 5% by weight based on the total weight of the formulation.

The personal care formulation according to the present invention may also contain one or more cationic ingredients. When present in the formulation, the or each cationic ingredient is preferably present at a concentration of between 0.01% and 10%, preferably between 0.05% and 8% and more preferably between 0.1% and 5% by weight based on the total weight of the formulation.

The personal care formulation according to the present invention may also contain one or more silicones. When present in the formulation, the or each silicone is preferably present at a concentration of between 0.05% and 10%, preferably between 0.1% and 8% and more preferably between 0.5% and 5% by weight based on the total weight of the formulation.

The personal care formulation according to the present invention may also contain one or more film forming components. When present in the formulation, the or each film forming component is preferably present at a concentration of between 0.01% and 5%, preferably between 0.05% and 3% and more preferably between 0.1% and 2% by weight based on the total weight of the formulation.

As has been described above, preferably the personal care formulation comprises no additional conditioning agents. However, in some alternative embodiments it may be possible to use additional conditioning agents. Such additional conditioning agents may be, for example, cationic polymers, including polyquaternium compounds, such as PQ-10, (provided that the polyquaternium compound does not contain any quaternised ammonium compounds having alkyl groups with carbon chains which are the same length as those present in the dialkyl amidoamine); and cationic guar.

Any of the above features may be taken in any combination and with any aspect of the invention.

EXAMPLES

The invention will now be illustrated further with reference to the following non-limiting examples. All parts and percentages are given by weight, based on the total weight of the material or composition as appropriate, unless otherwise stated.

Example 1: Oleic Acid—DETA Diamide

A pressure reactor fitted with nitrogen, vacuum, heating and cooling was charged with approximately 2 moles of Oleic acid and 1 moles of Diethylenetriamine (DETA). The vessel was sealed and heated to a temperature between 130° C. and 200° C. for 4 to 7 hours. Samples were taken over the course of the reaction and checked for acid value (AV) in a manner familiar to the person skilled in the art. Once an AV of <8 mg KOH was reached, the material was cooled and the product was also tested for By. The final BV obtained was 90.7 mg KOH.

Example 1a: Oleic Acid DETA Tertiary Amine

The resulting material from Example 1 was heated to between 90° C. and 120° C. in a a stainless steel pressure vessel and purged with nitrogen. Between 1-3 moles of Ethylene Oxide was slowly added to the vessel at a rate such as to maintain vessel pressure below 50 psi. Once all the EO was added, the reaction was allowed to continue for at least one hour and then the product was tested for tertiary amine content. The tertiary amine content was determined using AOCS method Tf 3a-64, and the final result obtained was >95%.

Example 2: Palm Oil—DETA Diamide

A pressure reactor fitted with nitrogen, vacuum, heating and cooling was charged with approximately 1 mole of Palm Oil and 1.5 moles of Diethylenetriamine (DETA). The vessel was sealed and heated to a temperature between of 130° C. and 200° C. for 4 to 7 hours. Samples of the reaction mixture were taken over the course of the reaction and checked for base value (BV) as known to one skilled in the art. Once the a BV of 89.2 mg KOH was reached the material was cooled.

Example 2a: Palm Oil—DETA Tertiary Amine

The resulting material from Example 2 was reacted to form the tertiary amine following the procedure outlined in Example 1a using 1-3 moles of Ethylene Oxide as the alkylating agent, until a tertiary amine content of >95% was reached.

Example 2b: Palm Oil—DETA Glycidol Tertiary Amine

The resulting material from Example 2 was reacted to form the tertiary amine following the procedure outlined in Example 1a using 1-3 moles of Glycidol as the alkylating agent, until a tertiary amine content of >95% was reached.

Example 3: Isostearic Acid—DETA Diamide

Following the same procedure as outlined in Example 1, approximately 2 moles of Isostearic acid and 1 mole of Diethylenetriamine (DETA) were reacted to form a diamide. The reaction was considered complete when an AV of <8 mg KOH and a BV of <90 was reached.

Example 3a: Isostearic Acid—DETA Tertiary Amine

The resulting material from Example 3 was reacted to form the tertiary following the procedure from Example 1a using of Ethylene Oxide as the alkylating agent until a tertiary amine content of >95% was reached.

Example 3b: Isostearic Acid—DETA Glycidol Tertiary Amine

The resulting material from Example 3 was reacted to form the tertiary following the procedure from Example 1a using 1-3 moles of Glycidol as the alkylating agent until a tertiary amine content of >95% was reached.

Example 4: High Erucic Rapeseed Oil (HEAR Oil)—DETA Diamide

A pressure reactor fitted with nitrogen, vacuum, heating and cooling was charged with approximately 1 mole of HEAR Oil and 1.5 moles of Diethylenetriamine (DETA). The vessel is then sealed and heated to a temperature between 130 C and 200 C for 4 to 7 hours. Samples are taken over the course of the reaction and checked for base value (BV) as known to one skilled in the art. Once a BV of 79.3 mg KOH was reached, the material was cooled.

Example 4a: High Erucic Rapeseed Oil (HEAR Oil) Tertiary Amine

The resulting material from Example 4 was reacted to form the tertiary following the procedure from Example 1a using 1-3 moles of Ethylene Oxide as the alkylating agent until a tertiary amine content of >95% was reached.

Examples 4b: High Erucic Rapeseed Oil (HEAR Oil) DETA Glycidol Tertiary Amine The resulting material from Example 4 was reacted to form the tertiary following the procedure from Example 1a using 1-3 moles of Glycidol as the alkylating agent until a tertiary amine content of >95% was reached.

Example 5: Hydrogenated High Erucic Rapeseed Oil (H2-HEAR Oil)—DETA Diamide

A pressure reactor fitted with nitrogen, vacuum, heating and cooling was charged with approximately 1 mole of H2-HEAR Oil and 1.5 moles of Diethylenetriamine (DETA). The vessel is then sealed and heated to a temperature between 130 C and 200 C for 4 to 7 hours. Samples are taken over the course of the reaction and checked for base value (BV) as known to one skilled in the art. Once a BV of 75 mg KOH was reached the material was cooled.

Example 5a: H2-HEAR Oil DETA Tertiary Amine

The resulting material from Example 4 was reacted to form the tertiary following the procedure from Example 1a using Ethylene Oxide as the alkylating agent until a tertiary amine content of >95% was reached.

Examples 5b: H2-HEAR Oil DETA Glycidol Tertiary Amine

The resulting material from Example 5 was reacted to form the tertiary following the procedure from Example 1a using Glycidol as the alkylating agent until a tertiary amine content of >95% was reached.

Example 6: Oleic/Palmitic/Linoleic Acid—DETA Diamide

A pressure reactor fitted with nitrogen, vacuum, heating and cooling was charged with approximately 2 mole equivalents of a blend of Oleic/Palmitic/Linoleic acids and 1 mole of Diethylenetriamine (DETA). The vessel is then sealed and heated to a temperature between 130 C and 200 C for 4 to 7 hours. Samples are taken over the course of the reaction and checked for base value (BV) and acid value (AV) as known to one skilled in the art. Once an AV of 8.8 mg KOH and a BV of 90.3 mg KOH was reached, the reaction was stopped and cooled.

Example 6a: Oleic/Palmitic/Linoleic Acid—DETA Diamide Tertiary Amine

The resulting material from Example 6 was reacted to form the tertiary following the procedure from Example 1a using Ethylene Oxide as the alkylating agent until a tertiary amine content of >95% was reached.

Example 7: Palm Oil (3,3-Diamino-N-Methyldipropylamine) Diamide

A pressure reactor fitted with nitrogen, vacuum, heating and cooling was charged with approximately 1 mole of Palm Oil and 1.5 mole of 3,3-Diamino-N-Methyldipropylamine. The vessel is then sealed and heated to a temperature between 130 C and 200 C for 4 to 7 hours. Samples are taken over the course of the reaction and checked for base value (BV). Once a BV of 81.47 was reached, the material was cooled.

Example 8: Hair Strengthening Creme Rinse

| Ingredients | % |
|---|---|
| PART A | |
| Deionized Water | 87.75 |
| Compound from Example 4b | 3.00 |
| CRODACOL S-70 (Stearyl Alcohol) (ex Croda) | 4.50 |
| SUPER STEROL ESTER ($C_{10-30}$ Cholesterol/Lanosterol Esters) (ex Croda) | 1.00 |
| Wheat Germ Oil | 1.50 |
| PART B | |
| KERAVIS (Hydrolyzed Vegetable Protein PG-Propyl Silanetriol) (ex Croda) | 1.00 |
| Propylene Glycol (and) Diazolidinyl Urea (and) Methylparaben (and) Propylparaben | 1.00 |

The ingredients of Part A were combined and heated to 75-80° C., while mixing until all solids were dissolved. The temperature was then held for 10 minutes, before the heat was removed and the mixture allowed to cool to 40° C. while mixing. The Part B ingredients were then added one at a time under continued mixing. The formulation was finally cooled to desired fill temperature.

Example 9: Low Cost Conditioner

| Ingredients | % |
|---|---|
| PART A | |
| Deionized Water | 94.90 |
| Lactic Acid | 0.10 |
| CRODACOL 1618 (Cetearyl Alcohol) (ex Croda) | 3.00 |
| Compound from Example 2a | 1.00 |
| PART B | |
| Phenoxyethanol (and) Propylparaben (and) Butylparaben (and) Methylparaben and Ethylparaben | 1.00 |

The Part A ingredients were combined and heated to 80° C. with mixing. Mixing continued at maintained heat for 10 minutes. The mixture was then removed from the heat and cooled to 40° C. The Part B ingredients were then added, mixing well. The pH was adjusted to between 4.3-5.0, if necessary, and the formulation mixed until smooth and homogeneous.

Example 10: Moisturizing Skin Lotion

| Ingredients | % |
|---|---|
| PART A | |
| Crodamol ISIS (Isostearyl Isostearate) (ex Croda) | 5.00 |
| Mineral Oil | 5.00 |
| Crodacol S-70 (Stearyl Alcohol) (ex Croda) | 2.52 |
| Compound from Example 6a | 2.50 |
| PART B | |
| Deionized Water | 76.98 |
| Lactic Acid | 0.22 |
| PART C | |
| Cyclomethicone | 2.0 |
| Propylene Glycol (and) Diazolidinyl Urea (and) Methylparaben (and) Propylparaben | 1.0 |

The ingredients of Part A were combined with mixing and heated to 75-80° C. The ingredients of Part B were combined and heated with mixing to 75-80° C. Part B was added to part A while mixing. The temperature was held for 15 minutes. The mixture of Part A and Part B ingredients was then allowed to cool to 50° C. and the Part C ingredients were added with mixing to form a homogeneous formulation.

Example 11: Hair Conditioner with UV Protection

| Ingredients | % |
|---|---|
| PART A | |
| Deionized Water | 88.28 |
| Lactic Acid | 0.22 |
| Chromaveil (Quaternium-95 (and) (Propanediol) (ex Croda) | 3.00 |
| CRODACOL 1618 (Cetearyl Alcohol) (ex Croda) | 5.00 |
| Compound from Example 1a | 2.50 |
| PART B | |
| Phenoxyethanol (and) Propylparaben (and) Butylparaben (and) Methylparaben and Ethylparaben | 1.00 |

The Part A ingredients were combined and heated to 80° C. with mixing. Mixing was continued and the heat maintained for 10 minutes. The heat was then removed and the mixture allowed to cool to 40° C. The Part B ingredients were then added, mixing well. The pH of the formulation was adjusted to 4-4.5 if necessary, and mixed until smooth and homogeneous.

Example 12: After Dye Conditioner

| Ingredients | % |
|---|---|
| PART A | |
| Deionized Water | 87.87 |
| Lactic Acid | 0.13 |
| INCROQUAT BEHENYL TMS-50 (Behentrimonium Methosulfate (and) Cetyl Alcohol (and) Butylene Glycol) (ex Croda) | 1.50 |
| CRODACOL 1618 (Cetearyl Alcohol) (ex Croda) | 5.00 |
| Compound from Example 3a | 1.50 |
| PART B | |
| Amodimethicone (and) Trideceth-12 (and) Cetrimonium Chloride | 3.00 |
| Phenoxyethanol (and) Propylparaben (and) Butylparaben (and) Methylparaben and Ethylparaben | 1.00 |

The Part A ingredients were combined and heated to 80° C. with mixing. The combined ingredients were mixed continuously whilst the heat was maintained for 10 minutes. The combination was then removed from the heat and cooled to 40° C. The Part B ingredients were added to the combination, mixing well. The pH of the formulation was adjusted to 4.0-4.5 if necessary and mixed until smooth and homogeneous.

Example 13: Hair Conditioner

| Ingredients | % |
|---|---|
| PART A | |
| Deionized Water | 94.39 |
| Lactic Acid | 0.11 |
| CRODACOL 1618 (Cetearyl Alcohol) (ex Croda) | 3.00 |
| Compound from Example 6a | 1.00 |
| Incromine BD (Behenamidopropyl Dimethylamine) (ex Croda) | 0.50 |
| PART B | |
| Phenoxyethanol (and) Propylparaben (and) Butylparaben (and) Methylparaben and Ethylparaben | 1.00 |

The Part A ingredients were combined and heated to 80° C. with mixing. The combined ingredients were mixed continuously whilst the heat was maintained for 10 minutes. The combination was then removed from the heat and cooled to 40° C. The Part B ingredients were added to the combination, mixing well. The pH of the formulation was adjusted to 4.0-4.5 if necessary and mixed until smooth and homogeneous.

Example 14: Hair Conditioning Coconut Oil

| Ingredients | % |
|---|---|
| Coconut Oil | 97.5-98 |
| Compound from Example 6a | 2 |
| Neutralizing agent (Optional) | Q.S. to 100 |

The coconut oil and the Example 6a compound were combined in the reaction vessel, and, if required, the neutralizing agent was added. The mixture was heated to 50° C. and mixed for 15 minutes, then pour into desired containers and allowed to cool.

Example 15: Wet and Dry Combing Test

The hair conditioner formulations A to G were prepared as set out in Table 1.

Each hair conditioner formulation was prepared by combining the Part A ingredients while mixing and heating to 75-80° C., and separately combining the Part B ingredients and heating to the same temperature. The Part A and Part B ingredients were then combined at temperature and allowed to cool to 40° C. Once at 40° C., the Part C ingredients were added and the pH adjusted to about 4.5 using lactic acid.

The following combing test procedure was carried out for each hair conditioner formulation A to G.

Combing Test Procedure

5 Dark bleached hair tresses available from International Hair Importers Inc., NYC, were cut to 1.3 cm wide and 20 cm long for each hair conditioner formulation A to G. The tresses were washed with global shampoo (SLES/Betaine shampoo) for 1 minute. Each tress was worked from top to bottom with thumb and fingers to avoid tangling. The tresses were then rinsed with running tap water for 1 minute. The tap water was allowed to run down each tress from top to bottom to avoid tangling. Once rinsed, the tresses were air-dried.

Baseline measurements of the wet and dry combing forces for all the hair tresses were measured before treatment.

After the baseline wet and dry measurements, each set of 5 hair tresses was treated with one of the hair conditioner formulations A to G. The treatment involved applying 2 grams of the hair conditioner formulation to each tress and allowing 3 minutes of treatment time—working the hair conditioner formulation on each hair tress for 1 minute, and then leaving it on for 2 minutes.

Once treated, the hair tresses were rinsed with running tap water for 1 minute and air-dried.

The following test procedures were then followed for each set of 5 hair tresses to measure the wet and dry combing forces for all the hair tresses after hair conditioner formulation treatment.

Procedure for Dry Combing Force Measurement

The hair tresses were placed into an environmental chamber to reach equilibrium for 2 hours. The temperature was set at 23° C. and relativity humidity set at 60%.

Each hair tress was combed manually 3-4 times using a wide- and narrow-toothed comb until no further tangling was noticed. First using the wide-tooth section and then using the narrow-tooth section.

Each hair tress was then clamped in the MTT combing accessory with the root end towards the jig. Using two fingers the hair tresses were flattened and pushed/guided into the comb attached on Dia-Stron. The dry combing force of each tress was then measured 10 times and the data collected.

The average of each 5-tress dry combing data for each hair conditioner formulation A to G was taken and ANOVA statistical analysis was run on the results to establish significance at 95% confidence. The results are shown in Table 2 below.

TABLE 2

Dry Comb results

| Formulation | % Change of Combing Force or Peak Load (gmf) | % Change of Total Work Done (Joules) |
|---|---|---|
| A | −85.84 +/− 1.40 | −52.53 +/− 1.74 |
| B | −82.56 +/− 2.11 | −54.41 +/− 3.16 |
| C | −85.90 +/− 4.05 | −64.42 +/− 14.48 |
| D | −87.72 +/− 11.12 | −69.39 +/− 10.30 |
| E | −93.08 +/− 0.86 | −69.41 +/− 2.57 |
| F | −73.30 +/− 11.02 | −49.41 +/− 11.71 |
| G | −85.52 +/− 4.70 | −61.17 +/− 6.57 |

Procedure for Wet Combing Force Measurement

A 1000 ml beaker was filled with 800 ml of de-ionized water. Each hair tress was submerged in the beaker 3 times.

The hair tresses were each combed manually with a wide- and narrow-toothed comb 3-4 times until no further tangling was noticed. First using the wide-tooth section and then using the narrow-tooth section.

TABLE 1

| | | | Formulation | | | | |
|---|---|---|---|---|---|---|---|
| | A | B | C | D | E | F | G |
| PART A | | | | | | | |
| Deionized Water | 93.775 | 92.775 | 95.78 | 95.4 | 94.45 | 94.50 | 95.4 |
| Lactic Acid | 0.125 | 0.125 | 0.10 | 0.40 | 0.40 | 4.10 | 0.40 |
| PART B | | | | | | | |
| Crodacol 1618* | 4.50 | 4.50 | 3.00 | 3.00 | 3.00 | 3.00 | 3.00 |
| Compound of Example 2b | 1.50 | 1.50 | — | — | — | — | — |
| 2a | — | — | 1.00 | — | — | — | — |
| 4a | — | — | — | 1.00 | — | — | — |
| 4b | — | — | — | — | 1.00 | — | — |
| 5a | — | — | — | — | — | 1.00 | — |
| 5b | — | — | — | — | — | — | 1.00 |
| Brij S10* | — | 1.00 | — | — | 1.00 | 1.00 | — |
| PART C | | | | | | | |
| Neolone 950** | 0.10 | 0.10 | 0.10 | 0.10 | 0.10 | 0.10 | 0.10 |
| Lactic Acid | q.s. | q.s. | 0.05 | 0.10 | 0.05 | 0.00 | 0.10 |
| pH (after 24 hours) | 4.46 | 4.21 | 4.68 | 4.64 | 4.49 | 4.54 | 4.63 |
| Viscosity (after 24 hours) | 55,500 cps | 49,500 cps | 4,500 cps | 6,000 cps | 15,500 cps | 4,500 cps | 4,500 cps |

*= ex Croda;
**= ex Dow

Each hair tress was submerged in the beaker once more and the excess water removed from the tress by lightly squeezing the top of the tress between the thumb and forefinger and moving them down the length of the tress.

Each hair tress was then clamped in the MTT combing accessory with the root end towards the jig. Two fingers were used to flatten the hair tress and push/guide it into the comb attached on Dia-Stron.

The wet combing force of each tress was measured 10 times using the Dia-Stron and the data collected. The average of each 5-tress wet combing data set for each hair conditioner formulation A to G was calculated and ANOVA statistical analysis run on the data to establish significance at 95% confidence. The results are shown in Table 3 below.

TABLE 3

Wet Comb results

| Formulation | % Change of Combing Force or Peak Load (gmf) | % Change of Total Work Done (Joules) |
|---|---|---|
| A | −96.51 +/− 0.49 | −94.86 +/− 0.74 |
| B | −93.24 +/− 1.01 | −93.31 +/− 0.76 |
| C | −96.70 +/− 1.20 | −96.85 +/− 0.93 |
| D | −97.61 +/− 0.30 | −97.64 +/− 0.19 |
| E | −98.04 +/− 0.56 | −97.77 +/− 0.41 |
| F | −65.61 +/− 6.68 | −83.54 +/− 2.73 |
| G | −79.34 +/− 6.00 | −90.04 +/− 1.97 |

The results indicate that each of the hair conditioner formulations A to G shows good wet-combing and dry-combing performance.

Example 16: Frizz Control Test

The formulations H to M as set out in Table 4 were prepared. Each hair conditioner formulation was prepared by combining the Part A ingredients while mixing and heating to 75-80° C., and separately combining the Part B ingredients and heating to the same temperature. The Part A and Part B ingredients were then combined while mixing at temperature and allowed to cool to 40° C. Once at 40° C., the Part C ingredients were added and the pH adjusted to about 4.5±0.5 using lactic acid.

Frizz Test Procedure

For each formulation H to M, 7 Brazilian curly hair tresses available from International Hair Importers Inc., NYC, were cut to 1.5 cm wide and 20 cm long.

The tresses were washed with a simple cleansing shampoo (SLES/Betaine shampoo) using a 1:10 w/w shampoo to hair ratio for 1 minute. The tresses were then rinsed with warm water for 1 minute or until free of foam. 3 g of the respective formulation was then massaged into the hair tresses for 1 minute. The treated tresses were left to sit for 20 minutes and then the formulations rinsed out of the hair for 45 seconds. Once rinsed, the tresses were blown dry using a blow dryer and round brush, and then flat-ironed using a ceramic iron at 400° F. for 5 passes. Initial photographs of each of the tresses were taken and the tresses were placed in humidity controlled environment at 75% RH and observed over time.

Pictures of 6 of the tresses evaluated from varied time points (4 hour, 24 hour, and 48 hour) were shown to a panel of 13 people. The panelists were asked to rank the tresses from 1 (least frizz) to 6 (most frizz). The mode and average of the panelists' rankings were calculated for each to give the overall ranking. Table 5 displays each total ranking based on the modes/averages and the percentage of panelists that agree with these rankings.

TABLE 4

Smoothing Conditioning Treatment Formulations

| | Formulation | | | | | |
|---|---|---|---|---|---|---|
| | H | I | J | K | L | M |
| | Amount (%) | | | | | |
| | Part A | | | | | |
| Water | 88.90 | 87.90 | 85.40 | 88.90 | 86.90 | 85.40 |
| | Part B | | | | | |
| Compound from example 3a | 0.00 | 1.00 | 3.50 | 1.50 | 3.50 | 5.00 |
| Incroquat TMS-50* | 3.00 | 3.00 | 3.00 | 0.00 | 0.00 | 0.00 |
| Bri jS20* | 2.50 | 2.50 | 2.50 | 2.50 | 2.50 | 2.50 |
| Mineral Oil | 2.00 | 2.00 | 2.00 | 2.00 | 2.00 | 2.00 |
| Crodacol CS50* | 3.50 | 3.50 | 3.50 | 5.00 | 5.00 | 5.00 |
| | Part C | | | | | |
| Neolone 950** | 0.10 | 0.10 | 0.10 | 0.10 | 0.10 | 0.10 |
| Lactic Acid | qs | qs | qs | qs | qs | qs |
| | 100.00 | 100.00 | 100.00 | 100.00 | 100.00 | 100.00 |

*= ex Croda;
**= ex Dow

TABLE 5

Total Ranking of Varied Time Points

| Ranking | Formulation | % of panellists agreeing with ranking |
|---|---|---|
| 1 | M | 100 |
| 2 | L | 85 |
| 3 | K | 51.3 |
| 4 | I | 37.8 |
| 5 | H | 80 |
| 6 | untreated | 89.7 |

Based on the ranking above, the following conclusions can be made:
1) All tresses treated with the Compound of Example 3a resisted frizz the best, with 100% of panelists agreeing that the tresses treated with 5% Compound 3a had the least frizz.
2) The addition of the Compound of Example 3a aids in frizz control, as 80% of panelists observed more frizz in the tresses treated with TMS-50 (Formulation H) alone.

The tress treated with Formulation I shows the least percent agreement because 33% of panelists ranked this tress as #3. The tress with Formulation K also shows less percent agreement because 38.5% of panelists ranked this tress as #4 indicating similar performance for the two tresses.

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A conditioning agent comprising at least 50% by weight based on the total weight of the conditioning agent of a dialkyl amidoamine which is the reaction product of
   a) a polyamine selected from diethylene triamine (DETA) and triethylene tetramine (TETA);
   b) a monocarboxylic acid that is isostearic acid, oleic acid, palmitic acid, linoleic acid or is obtained from palm oil, rape seed oil or HEAR (high erucic acid rape) oil; and
   c) an epoxide-containing compound selected from ethylene oxide, propylene oxide and glycidol,
   wherein tertiary amine content of the dialkyl amidoamine is >95% as determined using AOCS method Tf 3a-64, and
   wherein the conditioning agent is substantially free from quaternary ammonium compounds.

2. An anti-frizz agent comprising a dialkyl amidoamine which is the reaction product of
   a) a polyamine selected from diethylene triamine (DETA) and triethylene tetramine (TETA);
   b) a monocarboxylic acid that is isostearic acid, oleic acid, palmitic acid, linoleic acid or is obtained from palm oil, rape seed oil or HEAR (high erucic acid rape) oil; and
   c) an epoxide-containing compound selected from ethylene oxide, propylene oxide and glycidol,
   wherein tertiary amine content of the dialkyl amidoamine is >95% as determined using AOCS method Tf 3a-64, and
   wherein the anti-frizz agent is substantially free from quaternary ammonium compounds.

3. A predispersion or presolution comprising a conditioning agent of claim 1 and a dispersing agent or solvent or mixture thereof.

4. A method of conditioning hair, comprising applying the conditioning agent of claim 1 to the hair.

5. A method of reducing frizz in hair comprising applying the anti-frizz agent of claim 2 to the hair.

6. A predispersion or presolution comprising an anti-frizz agent of claim 2 and a dispersing agent or solvent or mixture thereof.

7. The conditioning agent of claim 1, wherein the polyamine is diethylene triamine (DETA).

8. The anti-frizz agent of claim 2, wherein the polyamine is diethylene triamine (DETA).

9. A personal care formulation comprising a conditioning agent of claim 1 and a viscosity modifier.

10. A personal care formulation comprising an anti-frizz agent of claim 2 and a viscosity modifier.

11. A personal care formulation according to claim 9, wherein the viscosity modifier is a fatty alcohol.

12. A personal care formulation according to claim 10, wherein the viscosity modifier is a fatty alcohol.

13. A personal care formulation comprising a conditioning agent of claim 1 and sodium lauryl ether sulphate or cocamidopropyl betaine.

14. A personal care formulation comprising an anti-frizz agent of claim 2 and sodium lauryl ether sulphate or cocamidopropyl betaine.

15. A hair care formulation comprising a conditioning agent of claim 1.

16. A hair care formulation comprising an anti-frizz agent of claim 2.

17. The conditioning agent of claim 1, wherein the polyamine is diethylene triamine (DETA), the monocarboxylic acid is from palm oil and the epoxide-containing compound is ethylene oxide.

18. The anti-frizz agent of claim 2, wherein the polyamine is diethylene triamine (DETA), the monocarboxylic acid is from palm oil and the epoxide-containing compound is ethylene oxide.

19. The conditioning agent of claim 1, wherein hair treated with the conditioning agent requires a lower combing force compared to untreated hair.

20. The conditioning agent of claim 1, wherein the treated hair is wet.

21. The conditioning agent of claim 1, wherein the treated hair is dry.

22. The anti-frizz agent of claim 2, wherein hair treated with the anti-frizz agent exhibits more frizz control compared to untreated hair.

* * * * *